United States Patent [19]
Christensen

[11] Patent Number: 5,360,394
[45] Date of Patent: Nov. 1, 1994

[54] RIGID JOINT SUPPORT BRACE SIZING MEANS AND METHOD

[76] Inventor: Roland J. Christensen, 192 East 1st North, Fayette, Utah 84630

[21] Appl. No.: 65,658

[22] Filed: May 21, 1993

[51] Int. Cl.[5] .............................................. A61F 5/00
[52] U.S. Cl. ...................................... 602/26; 602/13; 602/16; 126/DIG. 20; 2/22
[58] Field of Search ....................... 602/13, 16, 26, 20; 607/104, 108, 112; 126/DIG. 20; 2/22, 24, DIG. 3

[56] References Cited

U.S. PATENT DOCUMENTS

| | | |
|---|---|---|
| 3,786,804 | 1/1974 | Lewis . |
| 4,182,320 | 1/1980 | Sweeney . |
| 4,366,613 | 1/1983 | Nelson ............................ 2/24 X |
| 4,378,009 | 3/1983 | Rowley . |
| 4,628,945 | 12/1986 | Johnson . |
| 4,654,893 | 4/1987 | Meyers . |
| 4,802,466 | 2/1989 | Meyers et al. . |
| 4,803,975 | 2/1989 | Meyers . |
| 4,872,448 | 10/1989 | Johnson, Jr. . |
| 4,938,207 | 7/1990 | Vargo . |
| 5,125,400 | 6/1992 | Johnson . |
| 5,152,302 | 10/1992 | Fareed . |
| 5,230,695 | 7/1993 | Oliver et al. ...................... 602/13 |
| 5,230,696 | 7/1993 | Silver et al. ...................... 602/16 |

OTHER PUBLICATIONS

128/Dig. 20 Journal of Oalma, Aire-Fit Braces, May 1951.

Primary Examiner—Richard J. Apley
Assistant Examiner—Beverly A. Meindl
Attorney, Agent, or Firm—Thorpe, North & Western

[57] ABSTRACT

A removable rigid support brace for supporting a user's limb at a joint thereof comprises a rigid sheath member having an inner surface and sized to extend about and embrace the limb at the joint area. Hinging means disposed centrally in the sheath member enable the ends of the sheath member to pivot relative to each other and in concert with the joint movement. An array of individually adjustable and inflatable fluid filled chambers is mounted upon the inner surface of the sheath member to form a contained volume within said array for receiving the limb. The chambers are operable to customize a secure and comfortable fit of the rigid support brace to the contours of the limb and joint area.

18 Claims, 3 Drawing Sheets

RIGID JOINT SUPPORT BRACE SIZING MEANS AND METHOD

BACKGROUND OF THE INVENTION

The present invention relates to removable braces for supporting a user's limb at a joint thereof, such as the knee joint of a leg, and specifically to rigid and semi-rigid support braces.

Knee braces and the like are well known in the art for controlling and stabilizing a joint area in the event of an injury or other instability of the limb or the joint. Injuries to a joint area such as the straining or tearing of ligaments, tendons or cartilage occur when a limb becomes twisted, hyperextended or otherwise contorted into unnatural positions. These kinds of injuries are often the result of participation in athletic contests such as football and basketball, but they occur in a variety of ways. Of current interest are devices which can be worn by those who have sustained various knee injuries and which will both protect the knee against further injury, and support the injured or weakened knee sufficiently to allow one to resume activities on the playing field, in the work place, and so forth.

The prior art includes removable rigid support braces worn about the knee area. Such braces typically comprise a rigid sheath member approximately two feet long which conforms generally to the shape of a leg above and below the knee for placement about the knee area. The sheath member usually includes padding such as foam rubber on the inside to size the sheath to the leg and enable a somewhat comfortable fit. Such rigid sheaths are strong enough to resist sudden twisting, bending and so forth and thereby prevent hyperextension and other injurious lateral, fore and aft movement of the knee. Flexible braces have much less structural strength than rigid braces and are thus less effective in preventing hyperextension or other injurious knee movement.

The rigid brace currently available, however, are characterized by various disadvantages. The padding in rigid braces has only a limited capacity for sizing the sheath to the leg because the quantity of such padding is not continuously adjustable. If a user desires additional padding to improve the comfort or fit of the brace, none of the options presently available are very adequate. For example, a user may simply place additional padding, cloth or whatever soft material is readily available, between the brace and the leg. Such additional padding may thereafter fall out or shift about undesirably. It is also difficult to achieve a consistent fit from one use to the next in this manner. Further, rigid braces are unable to provide selectively adjustable stabilizing pressure to the knee, or different pressure to different points on the knee, which would be helpful in correcting knee instabilities and in achieving proper alignment of the knee during healing thereof.

The prior art includes various flexible knee braces which solve some of these problems, but introduce others. These braces typically include a flexible sleeve or sheath made of a suitable flexible fabric or elastic material and are thus much more comfortable and form-fitting than the rigid braces. The flexible fabric or elastic material from which they are made more ably adjusts and conforms to the contours of the limb than the padding in a rigid brace which is restrained by the rigid sheath.

However, although flexible knee braces more ably conform to leg size, they fail to provide the same degree of protection against hyperextension and other abnormal knee movement offered by rigid braces, because a flexible sheath or sleeve has much less strength than a rigid or semi-rigid sheath as discussed above. U.S. Pat. Nos. 3,786,804 and 4,938,207 attempt a solution to this problem by teaching a pair of flat vertical support arms, one such arm mounted upon each side of a flexible brace to provide some rigidity to the brace and to thereby protect against abnormal knee movement. However, although this approach does provide some protection against abnormal lateral movement, such protection is vastly inferior to that offered by a rigid or semi-rigid support brace which provides far more rigid structure than the support arms.

Users have thus had to choose between the comfort and adjustable fit offered by the flexible braces, and the superior protection against hyperextension and other abnormal lateral, fore and aft movement offered by the rigid braces.

Although the industry continues to research and develop devices for controlling instabilities in the knee and other joints, none of the braces known to applicant can single-handedly solve the problems discussed above. It is clear that there is a need for a joint-supporting brace which not only provides superior protection against hyperextension and other abnormal joint movement, but which can also customize a secure and comfortable fit to the limb, and which can be adjusted with respect to various leg sizes and contours.

OBJECTS AND SUMMARY OF THE INVENTION

It is therefore an object of the present invention to provide a rigid or semi-rigid brace for supporting a weakened or injured joint area of a limb.

It is also an object of the invention to provide such a brace for preventing hyperextension and abnormal lateral, fore and aft movement of the joint.

It is an additional object of the invention to provide such a brace which can be adjustably and comfortably fitted to the specific size and contours of various legs.

It is another object of the invention to provide such a brace by which substantially the same customized fit can be developed from one use to the next.

It is a further object of the invention to provide such a brace which is capable of selectively exerting pressure on predetermined regions of the knee in order to properly align the knee.

The above objects and others not specifically recited are realized in a specific illustrative embodiment of a rigid or semirigid knee brace for supporting a user's leg at the knee joint. The knee brace includes a rigid sheath member having an inner surface and sized to extend about and embrace the leg at the knee area. The sheath member includes two half-sections connected by a hinge pin to thereby enable the half-sections to pivot relative to each other and in concert with the knee movement. The sheath member further includes stopping means for limiting the pivoting action to thereby prevent hyperextensive or flexion movement of the knee, and fastening straps for frictionally engaging the sheath about the leg. An array of individually adjustable and inflatable fluid filled chambers is mounted upon the inner surface of the sheath to form a contained volume within the array for receiving the leg. The chambers include self-sealing valve means for selectively admitting and releasing fluid therefrom. The chambers are operable to customize a secure and comfortable fit of the brace to the contours of the leg and the knee area, and to exert selectively adjustable hydrostatic pressures on predetermined regions of the knee area to thereby align the knee.

In use, the brace is fastened to a user's leg to extend about and embrace the leg at the knee area. A fluid such as air is then selectively added to or removed from one or more chambers to comfortably size the brace to the contours of the leg and the knee area. Chambers positioned at or adjacent to a specific region of the knee can be selectively inflated to exert a greater or a lesser hydrostatic pressure to such region commensurate with the support and alignment needs thereof.

BRIEF DESCRIPTION OF THE DRAWINGS

The above and other objects, features and advantages of the invention will become apparent from a consideration of the subsequent detailed description presented in connection with the accompanying drawing in which.

DETAILED DESCRIPTION OF THE ILLUSTRATED EMBODIMENTS

Figure 1:
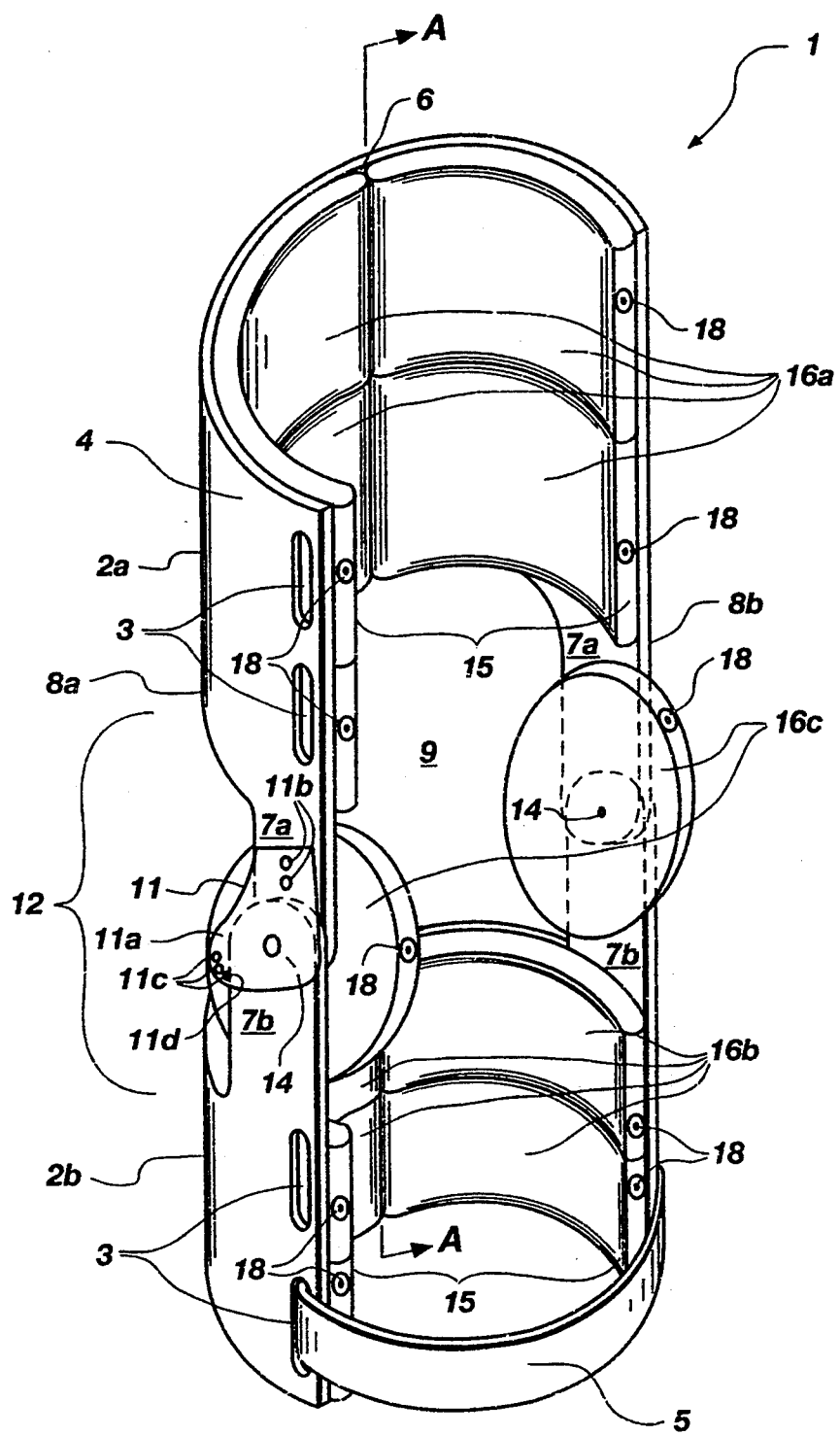
FIG. 1 is a perspective view of a knee brace made in accordance with the principles of the present invention.
Figure 2:
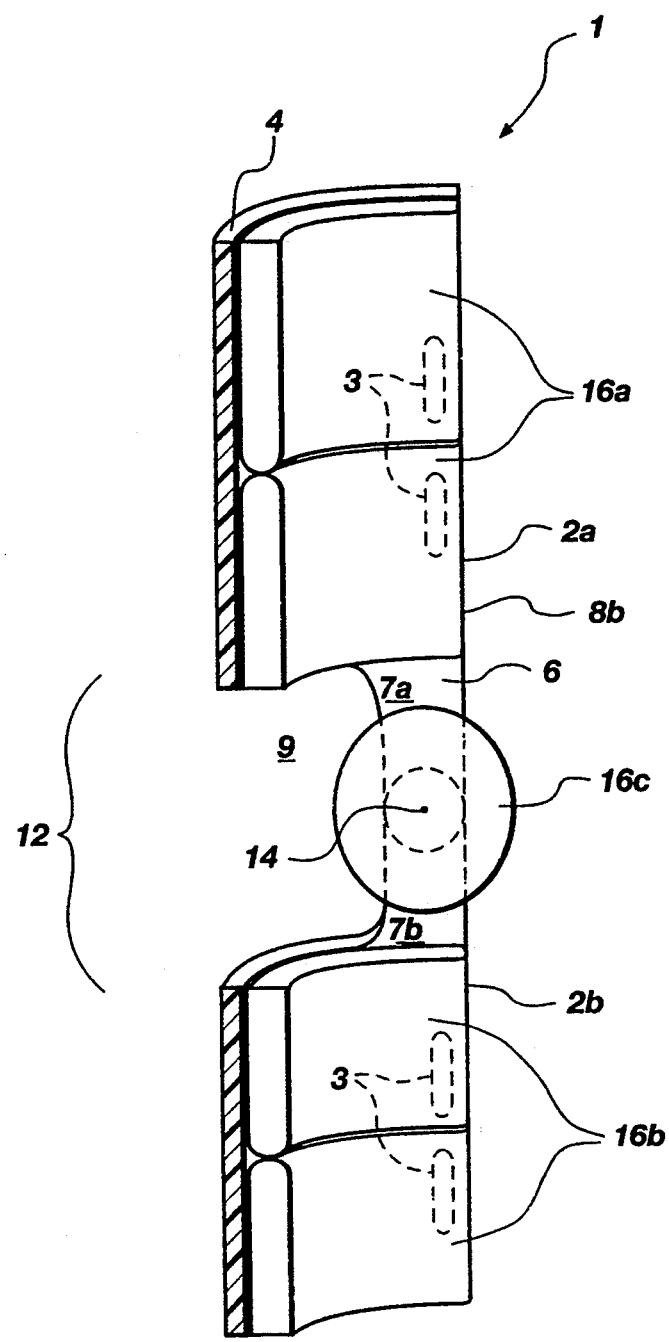
FIG. 2 is a side cross-sectional view of the knee brace of FIG. 1, taken along section A—A.

Referring to FIGS. 1-2, there is shown a knee brace generally designated at 1, which includes a continually rigid sheath member 4. Sheath member 4 includes upper-half-section 2a having upper arms 7a, and lower-half-section 2b having lower arms 7b, and defines a substantially semi-cylindrical inner surface 6 conforming to the shape of the enclosed leg. Portions of arms 7a–b are shown in phantom behind stopping plate 11a (see FIG. 1) and behind fluid chamber 16c (see FIG. 2). The sheath member 4 also has an open side 15, first and second sides 8a and 8b, and a central section 12 which includes an aperture 9. The sheath member 4 may be fabricated from a carbon-fiber graphite, formable plastic or other suitable rigid or semi-rigid material.

Two hinge pins 14 connect upper arms 7a to lower arms 7b to thereby join the half-sections 2a and 2b together and enable said half-sections to pivot relative to each other. The hinge pins 14 are typically two stainless steel pins. However, it will be understood that there are numerous alternative methods and apparatus which may be used to enable relative pivoting and displacement action of said half-sections 2a and 2b to mimic knee motion.

Stopping means 11 are disposed on the upper arms 7a of the sheath member 4 for limiting the pivoting action thereof to thereby prevent hyperextensive or flexion movement of the knee. FIG. 1 shows stopping means 11 which include stopping plate 11a attached to upper arm 7a by rivets 11b, degree stopping holes 11c and stopping peg 11d. The stopping peg 11d can be selectively inserted into one or two of said stopping holes 11c so that if the leg begins any undesired hyperextensive or flexion movement, the stopping peg 11d will abut the lower arm 7b to thereby prevent such hyperextensive or flexion movement. It will be understood that the stopping means 11 may embody the many forms known in the art and may be placed on the upper arms 7a of the sheath member 4 or on whatever location that will facilitate their purpose.

The sheath member 4 further includes slots 3 which receive fastening straps 5 for frictionally engaging the sheath member 4 about a user's leg (not shown) such that the sheath member 4 and the straps 5 together circumscribe the leg. The straps 5 are typically fabricated from a non-elastic nylon material and fastened with VELCRO (hook and loop) fastening surfaces, but may of course be made of an elastic or other suitable material and may utilize any conventional buckle or other fastening apparatus.

Referring still to FIGS. 1-2, an array of individually adjustable and inflatable fluid chambers 16a, 16b and 16c, having no fluid interconnection with each other, are mounted upon the inner surface 6 of the sheath member 4. The fluid chambers 16a–c are simply inflatable, air-tight pockets typically comprising a bladder made of urethane, or other flexible material, disposed within a cloth sleeve. Said fluid chambers 16a–c are typically inflated with air but can also be inflated with some other fluid, such as water, gelatin or other fluids.

Figure 3:
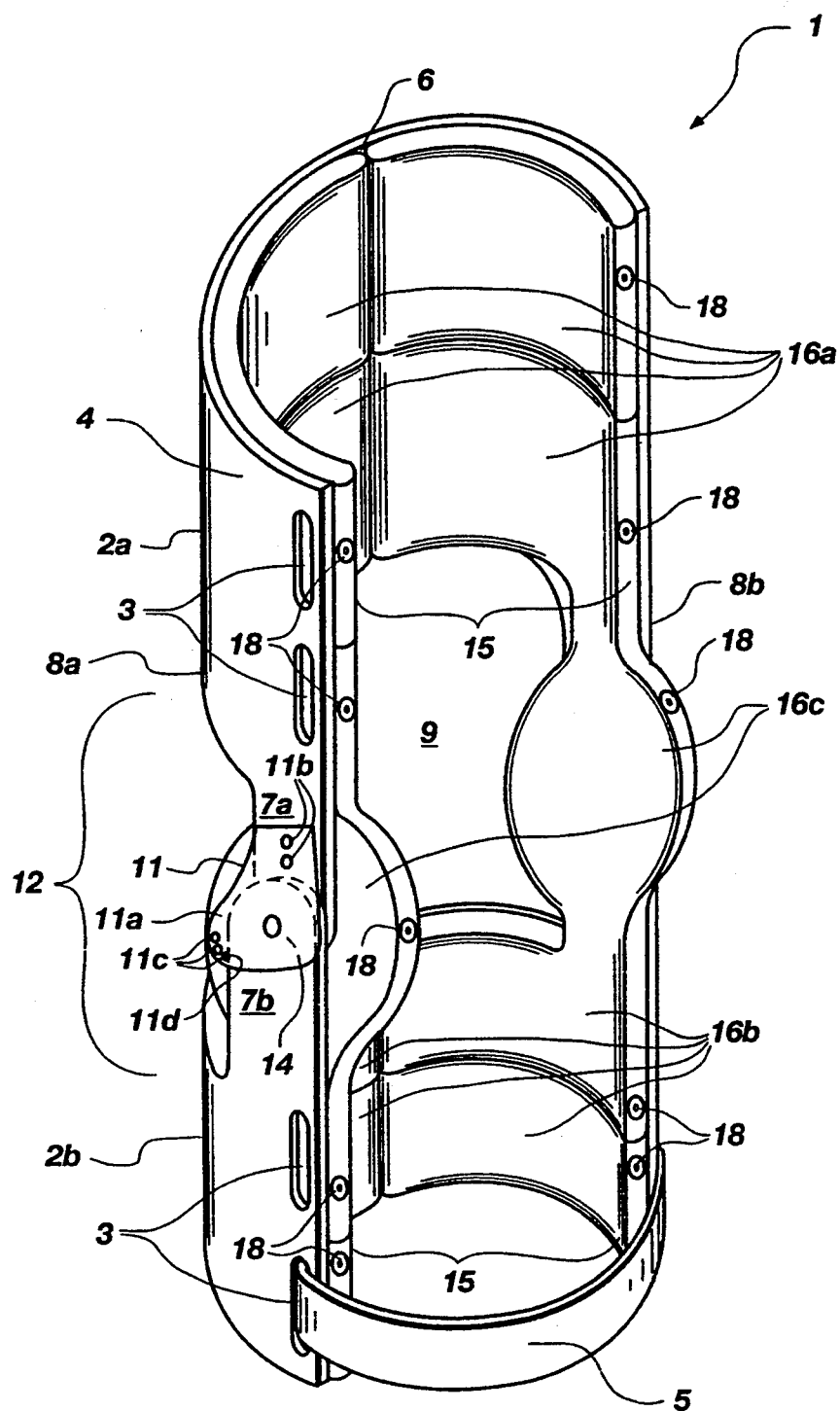
FIG. 3 is an alternative embodiment of the knee brace of FIG. 1.

Some or all of the fluid chambers 16a–c may alternatively be fluidly connected, one such arrangement being shown in FIG. 3 which shows the fluid chambers 16c fluidly connected with the lower fluid chambers 16a and the upper fluid chambers 16b. During use of the alternative embodiment of FIG. 3, when the user bends the knee, the volumes of the upper fluid chambers 16b and the lower fluid chambers 16a are decreased. Consequently, the fluid pressure in upper chambers 16b and lower chambers 16a increases, and the increase in pressure is distributed to the fluid chambers 16c. This pressure increase in the fluid chambers 16c is thus directed to the sides of the user's knee. Because of such varying pressures which result as the knee is flexed while using an embodiment having interconnected fluid chambers, a therapeutic massaging action is provided.

A preferred embodiment includes the fluid chambers 16a–c having no fluid interconnection with each other, being closely spaced and covering substantially the entire inner surface 6 of the sheath member 4 so as to form a contained volume within said array for receiving a leg (see FIG. 1). However, the fluid chambers 16a–c may also be spaced in any arrangement which suits the needs of the user. Referring to FIG. 1, it is noted that four fluid chambers 16a are located so as to be proximate to and above the knee cap, and four fluid chambers 16b are located so as to be proximate to and below the knee cap such that all said chamber 16a and 16b are substantially symmetrically positioned with respect to the knee cap or center of the leg. Two additional fluid chambers 16c are located at the sides 8 to cover portions of arms 7a and 7b so that each said chamber 16c is adjacent to one of the hinge pins 14 and proximate to the sides of the knee for a total of ten fluid chambers 16a–c.

The fluid chambers 16a–c are preferably fixed to the inner surface 6 with adhesive spray, hot glue, all-purpose rubber cement or other suitable adherent. However, it will be understood that the fluid chambers 16a–c may also be removably attached to the inner surface 6 with VELCRO fastening surfaces or other suitable means.

Each said fluid chamber includes a valve 18, preferably but not necessarily self-sealing, through which fluid is added to or released from each said chamber. The valves 18 are similar to small valves found in sports balls (basketballs). Air is pumped into or removed from each fluid chamber 16a, 16b or 16c in much the same way as air is pumped into or removed from a standard bicycle tire. Any conventional valve means known in the art could be used in place of the valves 18. As noted above, the fluid chambers 16a –c can also be filled with water, gelatin or other fluids. Additionally, heated or cooled fluids may be used to provide a therapeutic benefit which will be occasioned by the use of such fluids at the desired locations adjacent the knee joint.

A preferred method of use is as follows. When the brace 1 is assembled, it is placed onto a user's leg at the knee area such that the sheath member 4 and straps 5 circumscribe and frictionally engage the leg above and below the knee. The knee cap is allowed to protrude from the aperture 9 such that the sheath member 4 does not substantially contact or otherwise interfere with the knee cap. The hinge pins 14 enable the half-sections 2a and 2b to pivot relative to each other in concert with movement of the knee, and the stopping means 11 prevent hyperextensive or flexion knee movement. The user may selectively adjust the fluid chambers 16a–c to conform to the size and contours of the leg by either adding or removing air from one or more of said chambers to achieve a secure, comfortable fit. It is to be understood that the brace 1 may alternatively be removed from the leg while the fluid chambers 16a–c are being adjusted, if desired. The user may also adjust the fluid chambers 16a–c for the purpose of exerting hydrostatic pressure onto predetermined knee regions to thereby stabilize and align the knee.

One of ordinary skill in the art will appreciate the distinction between sizing the brace to a leg, and using the brace to exert hydrostatic pressure onto predetermined portions of a leg or knee. Sizing has more to do with fit and comfort, and is typically achieved by inflating the fluid chambers 16a–c with a moderate amount of fluid, enough so that said chambers will conform to the specific leg contours of the user but not so much that the user feels a tight squeeze or compression of the leg. In contrast, mild external pressure exerted upon a weakened region of a knee may enhance the healing process thereof. This is achieved by selectively adding more fluid to the fluid chamber corresponding to such weakened region, since the more fluid is added to said fluid chamber, the more pressure said fluid chamber exerts upon that portion of the knee or leg it contacts.

The user may also use the chambers 16a–c to properly align the knee by strategically positioning the brace 1 about the leg such that certain of the chambers 16a–c contact predetermined regions of the knee. The user can thereby counter any undesired turning or other movement of the knee during healing by increasing the pressure in the fluid chamber which contacts that portion of the knee prone to such movement. For example, referring to FIG. 1, if one of fluid chambers 16c and the fluid chamber 16a closest thereto were filled so as to have a greater pressure therein than the other chambers, said chambers would exert a correspondingly higher pressure to one side of the user's knee than would the other chambers to thereby achieve a desired alignment or stabilizing support of the knee.

The present invention represents a significant advance over traditional rigid braces. It is noted that many of the advantages of the present invention accrue due to the placement of individually adjustable fluid filled chambers on the inner surface of a rigid sheath member. The problem of customizing a secure and comfortable fit of the rigid sheath member to the leg is solved by the individually adjustable chambers. Although the foam-type padding in traditional rigid braces provides some comfort and sizing utility, the individually adjustable chambers of the present invention achieve vastly superior comfort and sizing utility by offering the additional feature of sizing adjustment and customization without sacrificing the advantages of a continually rigid sheath member, features lacking in traditional joint-supporting braces. An added advantage offered by the present invention is the capacity to selectively introduce a hydrostatic pressure on predetermined portions of the knee area or other portions of the leg without sacrificing the advantages of continuous structural rigidity of the brace. Those skilled in the art will appreciate from the preceding disclosure that the objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A removable brace for supporting a human limb at a joint thereof, the limb and the joint having contours, the brace comprising:

a rigid sheath member formed from first and second half-sections, having an inner surface and sized so as to extend about and embrace the limb at the joint area to thereby inhibit abnormal movement of the joint and the limb, the sheath member having an open side to enable entry of the limb thereto and further including sides and a central section;

hinging means disposed in the central section of the sheath member to enable the first and second half-sections of said sheath member to move relative to each other in concert with movement of the joint;

a plurality of individually adjustable and inflatable fluid filled chambers mounted upon the inner surface of the sheath member, said chambers being operable to customize a secure and comfortable fit of the brace to the contours of both the limb and the joint area, and further to enable each chamber to exert a selectively adjustable hydrostatic pressure on predetermined portions of the limb to thereby support and align the joint; and attachment means secured to the sheath member for releasably attaching said sheath member about the joint area of the limb wherein the plurality of fluid filled chambers is an array of fluid filled chambers mounted upon substantially the entire inner surface of the sheath member to form a contained volume with said array for receiving the limb.

2. A brace as in claim 1 wherein said fluid filled chambers are removably mounted upon said inner surface.

3. A brace as in claim 1 wherein said fluid filled chambers are substantially continuous across said inner surface.

4. A brace as in claim 1 wherein said fluid filled chambers further comprise self-sealing valve means for selectively admitting and releasing fluid with respect to each said chamber to thereby permit the hydrostatic pressure exerted by each said chamber on the leg to be either increased or decreased in order to achieve a predetermined pressure.

5. A brace as in claim 1, the attachment means comprising adjustable fastening straps secured to the sides of the sheath member to thereby span the open side of said sheath member and adapted to frictionally engage the leg above and below the knee such that the sheath member and the straps together circumscribe the leg.

6. A brace as in claim 1, the attachment means comprising elastic fastening straps secured to the sheath member and adapted to frictionally engage the leg above and below the knee such that the sheath member and the straps together circumscribe the leg.

7. A brace as in claim 1 wherein the central section of the sheath member includes an aperture located so as to allow the knee cap to protrude from the sheath member such that the sheath member does not substantially contact the knee cap.

8. A brace as in claim 1, the hinging means comprising:
first hinge disposed in one side of the sheath member at said central section and located so as to face one side of the knee; and
second hinge disposed in the opposite side of the sheath member at said central section and located so as to face the opposite side of the knee.

9. A brace as in claim 8, the array of fluid filled chambers further comprising:
at least one individually adjustable and inflatable fluid filled chamber mounted upon the portion of the inner surface of the sheath member corresponding to said first hinge; and
at least one individually adjustable and inflatable fluid filled chamber mounted upon the portion of the inner surface of the sheath member corresponding to said second hinge.

10. A brace as in claim 8 wherein the array of fluid filled chambers comprises:
first, second, third and fourth closely spaced fluid filled chambers located so as to be proximate to and above the knee cap during use and symmetrically arranged with respect to the knee cap in two rows of two chambers each; and
fifth, sixth, seventh and eighth closely spaced fluid filled chambers located so as to be proximate to and below the knee cap during use and symmetrically arranged with respect to the knee cap in two rows of two chambers each, said first, second, third, fourth, fifth, sixth, seventh and eighth chambers having no fluid interconnection with each other.

11. A brace as in claim 10, wherein the array of fluid filled chambers further comprises:
ninth and tenth fluid filled chambers mounted upon portions of the inner surface of the sheath member corresponding to the first and second hinges.

12. A brace as in claim 11 wherein there is fluid interconnection between one or more of said fluid filled chambers and side chambers.

13. A brace as in claim 1 wherein the fluid comprises air.

14. A brace as in claim 1 wherein the sheath member further comprises stopping means disposed on the sheath member for limiting the range of pivoting motion of said half-sections to thereby prevent hyperextensive or flexion movement of the knee.

15. A method for selectively sizing a removable support brace about a limb at a joint area thereof, the joint having a tip when bent, the limb and the joint area having contours, the method comprising the steps of:
a) selecting a rigid sheath member formed from first and second half-sections, the sheath member having a centrally located aperture, an inner surface and sized so as to extend about and embrace the limb at the joint area to thereby inhibit hyperextension and other abnormal movement of the joint and the limb, the sheath member having an open side to enable entry of the limb thereto and further including sides and a central section;
b) securing fastening straps to the sides of the sheath member above and below the portion of the sheath member corresponding to the knee area such that said straps span the open side of said sheath member;
c) mounting a plurality of fluid chambers upon the inner surface of the sheath member to form a an array of fluid filled chambers upon substantially the entire inner surface of the sheath member to form a contained volume within said array for receiving the limb, said chambers being operable to achieve a secure and comfortable fit of the brace to the contours of both the limb and the joint area, and further to enable each chamber to exert a selectively adjustable hydrostatic pressure on predetermined portions of the limb;
d) inflating the fluid chambers with a fluid so that each chamber exerts a selectively adjustable hydrostatic pressure on predetermined portions of the limb when the brace is placed thereon to thereby customize a secure and comfortable fit of the brace to the contours of both the limb and the joint area;
e) placing the support brace onto the limb such that the brace extends about and embraces the limb at the joint area and permits the tip of the joint to protrude from the aperture member without substantially contacting the sheath member;
f) fastening the straps such that the sheath member and the straps together circumscribe and frictionally engage the limb; and
g) adjusting the hydrostatic pressure exerted by one or more of said fluid chambers by selectively adding or removing fluid therefrom to thereby customize the fit of the brace to the limb, to enable a proper alignment of the knee and knee cap during healing of the limb or the joint area, and further to avoid the inhibition of natural healing movement of the knee area.

16. A method according to claim 15, wherein the support brace is a knee brace, the limb is a leg having a knee and knee cap, the step of placing further comprising the following step:
placing the knee brace onto the leg such that the brace extends about and embraces the leg at the knee area and permits the knee cap to protrude from the aperture without substantially contacting the sheath member.

17. A method according to claim 15 wherein the step of adjusting the hydrostatic pressure further comprises the steps of:
removing the brace from the limb;
adjusting the hydrostatic pressure as described; and
placing the brace back onto the limb as before.

18. A method according to claim 15 further comprising the steps of:
mounting at least one fluid chamber to a first hinge disposed in one side of the sheath member at said central section, said fluid chamber located so as to face one side of the knee; and
mounting at least one fluid chamber to a second hinge disposed in the opposite side of the sheath member at said central section, said fluid chamber located so as to face the opposite side of the knee.

* * * * *